United States Patent [19]

Von Esch et al.

[11] 4,007,185
[45] Feb. 8, 1977

[54] 3,5-SUBSTITUTED-1,2,4-OXADIAZOLE INNER QUATERNARY AMMONIUM SALTS

[75] Inventors: Anne Mary Von Esch, North Chicago; Aldo Joseph Crovetti, Lake Forest, both of Ill.

[73] Assignee: Abbott Laboratories, North Chicago, Ill.

[22] Filed: May 22, 1975

[21] Appl. No.: 580,085

Related U.S. Application Data

[62] Division of Ser. No. 316,189, Dec. 18, 1972, Pat. No. 3,907,809, which is a division of Ser. No. 85,747, Oct. 30, 1970, Pat. No. 3,725,424.

[52] U.S. Cl. .................................. 260/251 R
[51] Int. Cl.² ...................................... C07D 271/06
[58] Field of Search .................. 260/251 R, 307 G

[56] References Cited

UNITED STATES PATENTS

| | | | |
|---|---|---|---|
| 3,096,332 | 7/1963 | Von Esch et al. | 260/251 R |
| 3,478,049 | 11/1969 | Von Esch et al. | 260/251 R |
| 3,557,099 | 1/1971 | Breuer | 260/307 G |
| 3,651,054 | 3/1972 | Crovetti et al. | 260/307 G |
| 3,720,668 | 3/1973 | Breuer | 260/307 G |

Primary Examiner—Paul M. Coughlan, Jr.
Attorney, Agent, or Firm—Vincent A. Mallare; Robert L. Niblack

[57] ABSTRACT

New antimicrobial agents of the formula

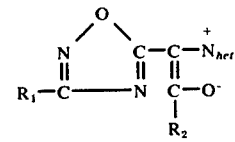

where $R_1$ includes halophenyl, loweralkyl, phenyl, nitrophenyl, dinitrophenyl, nitrofuryl, and nitrothienyl; $R_2$ includes hydrogen and loweralkyl; and $N_{het}$ includes a heterocyclic moiety bonded through a nitrogen thereof which is sufficiently basic to form quaternary ammonium salts.

1 Claim, No Drawings

3,5-SUBSTITUTED-1,2,4-OXADIAZOLE INNER QUATERNARY AMMONIUM SALTS

This is a division of application Ser. No. 316,189 filed Dec. 18, 1972, now U.S. Pat. No. 3,907,809, and which was a divisional of Ser. No. 85,747 filed Oct. 30, 1970, now U.S. Pat. No. 3,725,424.

DISCLOSURE OF THE INVENTION

This invention relates to new compounds having antimicrobial utility and which have the formula

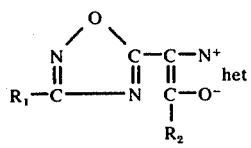

wherein $R_1$ is loweralkyl, phenyl, nitrophenyl, dinitrophenyl, nitrofuryl, and nitrothienyl; $R_2$ is hydrogen and loweralkyl; and $N_{het}$ is a heterocyclic moiety bonded to the carbon atom on the 5-position of the oxadiazole through a nitrogen atom thereof, which nitrogen is sufficiently basic to quaternize. Such groups that are suitable include pyridinyl, halo and loweralkyl substituted pyridinyl; pyrimidinyl, halo and loweralkyl substituted pyrimidinyl, quinolinium, halo and loweralkyl substituted quinolinium, isoquinolinium, halo and loweralkyl substituted isoquinolinium, thiazolium, isothiazolium and loweralkylthiazolium.

As used herein, the term "loweralkyl" is intended to include those alkyl groups having from 1 to 4 carbon atoms, e.g., methyl, ethyl, propyl and butyl. The term 'halo' is meant to include halogen substitutions wherein the halogen substituent is chlorine, bromine, or iodine.

The novel salts of this invention which are described below in detail possess valuable antibiotic activity against organisms such for example as *Staphylococcus aureus*. Furthermore, activity has been established for a number of these new compounds (as shown below in Table II) against the pathogenic fungi of the genus Trichomona especially *T. vaginalis*.

These new compounds are utilized as the inner quaternary salt, and being such are somewhat water soluble, at least more so than non-salt organic compounds of an equivalent molecular weight. They may be used in human and veterinary medicine in the form of pharmaceutical compositions containing one or more pharmaceutical carriers or excipients suitable, for example, for oral, topical, rectal, intravaginal or parenteral administration. They may be used alone or together with other medicinal agents. The compositions are preferably in unit dosage form and each dosage unit preferably contains 0.5 to 500 mg. of the active compound, advantageously 5 to 250 mg. for example.

For administration as solid oral preparations such as tablets or capsules, conventional carriers may be employed, for example, gelatin, lactose, starch, talc, magnesium stearate, hydrogenated oils, polyglycols, etc. The compositions may also take the form of liquid oral preparations for ingestion such as solutions, syrups, elixirs, emulsions, etc., which may contain suspending, emulsifying, stabilizing and preserving agents and may also contain acceptable sweetening, flavoring or coloring agents. The compounds may be prepared for local application to the mucous membranes of the nose and throat and may take the form of liquid sprays or powder insufflations, nasal drops, throat paints or similar preparations. Formulations for external applications may be prepared in oily, aqueous or powdered media in the form of conventional skin paints, lotions, creams, ointments, aerosols, dusting powders, etc. Suppositories and pessaries may contain a conventional base, e.g., oil of theobroma, polyglycols, glycogelatin bases together with surface active agents if required. The injectable preparations may take the form of aqueous or oily solutions, emulsions, suspensions or solids for reconstitution before use. Suitable vehicles include, for example, sterile, pyrogen-free water, parenterally acceptable oils, oily esters or other non-aqueous media such as propylene glycol, if desired containing suspending, dispersing, stabilizing, preserving, solubilizing, emulsifying or buffering agents.

The compounds of this invention are prepared most advantageously in the following manner. A compound of the formula

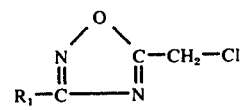

is admixed with $N_{het}$ where $R_1$ and $N_{het}$ are as hereinbefore defined, and an appropriate acid anhydride. By appropriate acid anhydride, it is meant that if $R_2$ is intended to be hydrogen, then a mixed acetic-formic anhydride should be used, and if $R_2$ is to be isopropyl, then 2,2-dimethyl-acetic anhydride should be employed. While the reaction can be carried out without the use of additional solvent, preferably an inert solvent such as nitromethane, ethanol or aqueous dimethylsulfoxide is used to insure a more complete reaction with higher yields. By the term "inert solvent", is meant a solvent that is not reactive toward reactants or products.

The reaction can be carried out at the reflux temperature of the admixture; yet it is preferred that the reaction temperature be maintained between 25°–75° C. The course of the reaction can easily be followed by observing the formation of product which is a brightly colored solid. After reaction is deemed complete, which is usually the case after 12 hours, the solid product is collected and washed, for example with cold, i.e., less than 0° C. ethanol.

The following specific examples will further serve to illustrate this invention.

EXAMPLE 1

In this method of preparation, the reactants act as mutual solvents, no additional solvent being added. Thus, 9.2 g. of 5-chloromethyl-3-(5-nitro-2-furyl)-1,2,4-oxadiazole was dissolved in a mixture of 10 ml. of acetic anhydride and 25 ml. of pyridine. The solution was heated overnight at 55° C. In the course of the reaction, the product crystallizes as a bright yellow solid. The compound was filtered and washed with ethanol. The yield is 12.5 g., m.p. 265° C (dec). For analysis the compound can be recrystallized from nitromethane or ethanol.

Analysis Calcd. for $C_{14}H_{10}N_4O_5$: C,53.51%; H,3.21%; N,17.82%.

Found: C,53.24%; H,3.22%; N,17.83.

EXAMPLE 2

In this preparation, additional solvent herein being acetonitrile is added. Thus, 5.0 5. (0.0218 mole) of 5-chloromethyl-3-(5-nitro-2-furyl)-1,2,4-oxadiazole, 2.03 g. (0.0218 mole) of 4-methylpyridine, 2.80 g. of acetic anhydride in 25 ml. acetonitrile heated at reflux for 2 hours. The reaction is cooled, the product filtered, washed with acetonitrile and alcohol successively. After having been dried, there was about 3 g. of crude product having a melting point of greater than 300° C.

Examples 3 through 24 are described in tabular form. In Examples 23 and 24, acetonitrile was utilized as the solvent for the reaction. In Examples 3–22, the reactants served as solvent, no additional solvent being utilized. Other than the different identity of the reactants, and the use of solvents, the methods used in Examples 3 through 24 were completely analogous to the above Examples.

| Ex. No. | $R_1$ | $N_{het}$ | $R_2$ | M.P. in °C | Solvent for Recrystallization | % yield |
|---|---|---|---|---|---|---|
| 3 | $CH_3$ | pyridinium | $-CH_3$ | 240–242 (dec) | ethanol | 73.3 |
| 4 | phenyl | pyridinium | $-CH_3$ | 196 (dec) | ethanol | 82.6 |
| 5 | 4-nitrophenyl | pyridinium | $-CH_3$ | 272–277 (dec) | nitromethane | 71.5 |
| 6 | 2,4-dinitrophenyl | pyridinium | $-CH_3$ | 260 (dec) | ethanol | 75.5 |
| 7 | 5-nitro-2-thienyl | pyridinium | $-CH_3$ | 248–250 (dec) | ethanol | 83.3 |
| 8 | 5-nitro-2-furyl | pyridinium | $-CH_3$ | 265 (dec) | nitromethane | 97.3 |
| 9 | 5-nitro-2-furyl | pyridinium | $-CH_2CH_3$ | 243–245 (dec) | nitromethane | 98 |
| 10 | 5-nitro-2-furyl | pyridinium | $-CH_2CH_2CH_3$ | 253 | ethanol | 80.5 |
| 11 | 5-nitro-2-furyl | 2-methylpyridinium | $-CH_3$ | 247–249 (dec) | ethanol | 72 |
| 12 | 5-nitro-2-furyl | 3-methylpyridinium | $-CH_3$ | 255–258 (dec) | nitromethane | 50 |
| 13 | 5-nitro-2-furyl | 4-methylpyridinium | $-CH_3$ | 300 (dec) | nitromethane | 73 |
| 14 | 5-nitro-2-furyl | 2,3-dimethylpyridinium | $-CH_3$ | 235 (dec) | nitromethane | 37 |
| 15 | 5-nitro-2-furyl | 2,4-dimethylpyridinium | $-CH_3$ | 245–247 (dec) | nitromethane | 89 |

-continued

| Ex. No. | R₁ | N_het | R₂ | M.P. in °C | Solvent for Recrystallization | % yield |
|---|---|---|---|---|---|---|
| 16 | 5-nitrofuran-2-yl | 3,5-dimethylpyridinium (−N⁺) | −CH₃ | 295 (dec) | nitromethane | 67 |
| 17 | 5-nitrofuran-2-yl | 2,6-dimethylpyridinium (−N⁺) | −CH₃ | 245–247 (dec) | nitromethane | 69 |
| 18 | 5-nitrofuran-2-yl | 2,4-dimethylpyridinium (−N⁺) | −CH₃ | 290 (dec) | nitromethane | 99 |
| 19 | 5-nitrofuran-2-yl | 3,4-dimethylpyridinium (−N⁺) | −CH₃ | 300 (dec) | ethanol | 51.5 |
| 20 | 5-nitrofuran-2-yl | isoquinolinium (−N⁺) | −CH₃ | 255 (dec) | nitromethane | 41.8 |
| 21 | 5-nitrofuran-2-yl | 4-methylquinolinium (−N⁺) | −CH₃ | >300 (dec) | nitromethane | 24 |
| 22 | 5-nitrofuran-2-yl | 3-bromopyridinium (−N⁺) | −CH₃ | 247–249 (dec) | nitromethane | 63.7 |
| 23 | 5-nitrofuran-2-yl | 3-carbamoylpyridinium (−N⁺) | −CH₃ | 283–284 (dec) | DMSO + H₂O | 45 |
| 24 | 5-nitrofuran-2-yl | 4-carbamoylpyridinium (−N⁺) | −CH₃ | 270 (dec) | DMSO + H₂O | 85 |

The 5-chloromethyl-3-(3,5-dinitrophenyl)-1,2,4-oxadiazole, which is used to prepare the compound of this invention disclosed in Example 6, is prepared in the following manner:

10 g. of 3,5-dinitrophenylamidoxime is refluxed in 20 ml. of chloroacetylchloride for two hours. The excess acid chloride is removed under reduced pressure. The oily solid is then suspended in 50 ml. of butanol and refluxed for six hours. Upon cooling, the product crystallizes from the solvent. M.P. 126°–8° C.

Analysis Calcd. for $C_9H_5ClN_4O_5$: C,37.99; H,1.78; H,19.66. Found: C,38.16; H,1.77; N,19.75.

The compounds of this invention have demonstated in vitro utility against *Staphylocossus aureus* Smith and such activity is illustrated in Table I in which the minimum inhibitory concentration is set forth in parts per million.

Table I

| Compound of Example | Minimum Inhibitory Concentration |
|---|---|
| 14 | 10 |
| 15 | 100 |
| 16 | 100 |
| 17 | 100 |
| 18 | 100 |
| 19 | 10 |
| 20 | 100 |

Table II illustrates the in vitro activity of the compounds of this invention against *Trichomonas vaginalis* in parts per million.

Table II

| Compound of Example | Minimum Inhibitory Concentration |
|---|---|
| 7 | 100 |
| 10 | 100 |
| 11 | 100 |
| 15 | 100 |

Table II-continued

| Compound of Example | Minimum Inhibitory Concentration |
| --- | --- |
| 19 | 10 |
| 20 | 10 |

We claim:

1. The compound of the formula

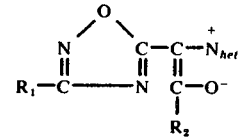

in which $N_{het}$ is selected from the group consisting of pyrimidinyl; halo and loweralkyl substituted pyrimidinyl; $R_1$ is selected from the group consisting of loweralkyl, phenyl nitrophenyl, dinitrophenyl, nitrofuryl, and nitrothienyl; and $R_2$ is selected from the group consisting of hydrogen and a loweralkyl wherein said loweralkyl groups have from 1–4 carbon atoms.

* * * * *